United States Patent [19]

Petzoldt et al.

[11] Patent Number: 5,403,724
[45] Date of Patent: Apr. 4, 1995

[54] MICROBIOLOGICAL REDUCTION OF PROSTACYCLIN INTERMEDIATE PRODUCTS WITH A 15-KETO GROUP

[75] Inventors: Karl Petzoldt; Helmut Dahl; Werner Skuballa, all of Berlin, Germany

[73] Assignee: Schering Aktiengesellschaft, Berlin and Bergkamen, Germany

[21] Appl. No.: 176,927

[22] Filed: Jan. 3, 1994

Related U.S. Application Data

[63] Continuation of Ser. No. 986,818, Dec. 8, 1992, abandoned, which is a continuation of Ser. No. 733,528, Jul. 22, 1991, abandoned, which is a continuation of Ser. No. 25,294, Jan. 27, 1987, abandoned.

[51] Int. Cl.⁶ .................... C12P 31/00; C12N 1/14
[52] U.S. Cl. ..................... 435/63; 435/254.22; 435/911; 435/921
[58] Field of Search .............. 435/63, 254.22, 911, 435/921

[56] References Cited

U.S. PATENT DOCUMENTS 4,247,635  1/1981  Kieslich et al. ................... 435/63

OTHER PUBLICATIONS

Koch et al., Chem. Ber., 103:603–609 (1970).
*The Yeasts*: A Taxonomic Study, J. Lodder, ed., Delft, The Netherlands, pp. 226–241 and 893–898 (1970).
ATCC Catalogue of Fungi, pp. 183, 289 (1982).

*Primary Examiner*—Irene Marx
*Attorney, Agent, or Firm*—Millen, White, Zelano & Branigan

[57] ABSTRACT

A process for production of 15-alpha-hydroxyprostaglandin intermediates of formula I

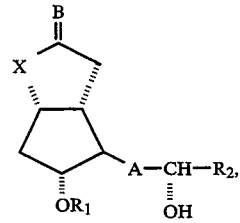

wherein
X is $CH_2$,
A is trans —CH=CH—
B is ethylenedioxy or 2,2-dimethylpropylenedioxy,
$R_1$ is benzoyl, and
$R_2$ is

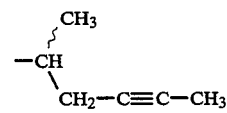

by treating a ketone of formula II

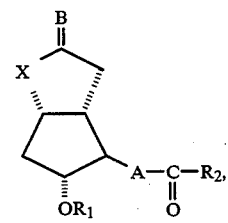

wherein A, B, X, $R_1$ and $R_2$ have the meanings indicated above, with a culture of *Candida solani* (NCYC 41) and isolating the resulting 15-alpha-hydroxyprostaglandin intermediate.

2 Claims, No Drawings

MICROBIOLOGICAL REDUCTION OF PROSTACYCLIN INTERMEDIATE PRODUCTS WITH A 15-KETO GROUP

This application is a continuation of application Ser. No. 07/986,818, filed Dec. 8, 1992, now abandoned, which is a continuation of Ser. No. 07/733,528, filed Jul. 22, 1991, now abandoned, which is a continuation of Ser. No. 07/025,294, filed Jan. 27, 1987, now abandoned, which is based on international application PCT/DE86/00213 filed May 16, 1986.

The invention relates to a microbiological process for enantioselective reduction of the 15-keto function in bicyclic prostacyclin intermediate products to the corresponding 15 alpha hydroxy compounds.

The invention is particularly suitable for microbiological reduction of the prostacyclin intermediate stages 1 to 6 listed below.

1
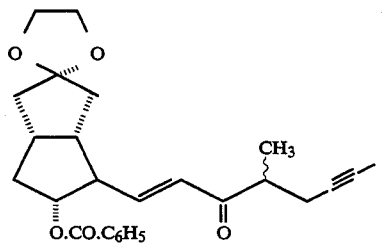

2
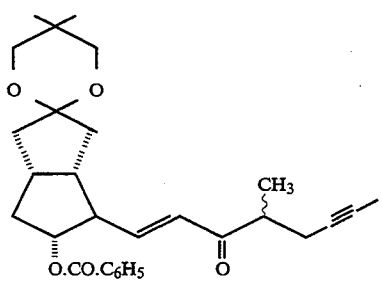

3
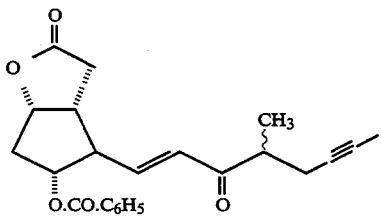

4
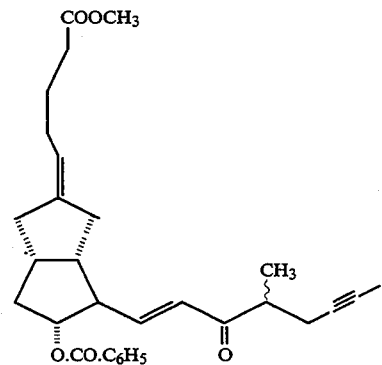

5
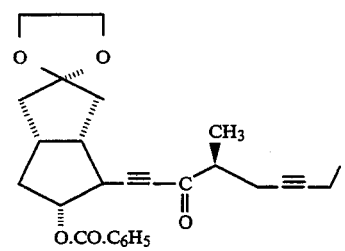

6
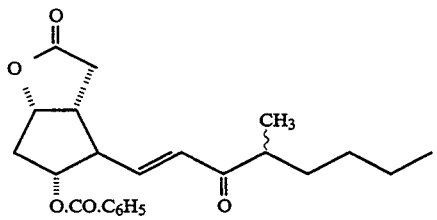

The microbiological reduction according to the invention of the above listed prostacyclin intermediate products is performed with the following microorganism strains: *Candida solani* (NCYC 41), *Pichia farinosa* (NRRL-y-118) and *Pichia farinosa* (CBS 185). Of these strains *Candida solani* has proved particularly successful.

The following prior art is known from EP 12710: While the chemical reduction of the 15-keto groups in prostaglandins and prostaglandin intermediate products, for example, with sodium borohydride only with mixtures of the corresponding 15 alpha and 15 beta hydroxy compounds and because of the attendant separation leads to the desired 15 alpha hydroxyprostaglandins only with yield losses, by U.S. Pat. No. 3,687,811 a series of microorganism are known which convert the 15-keto group in 11-hydroxy 15-oxo-prostaglandins, depending on the already present conformation of the 11-hydroxy group, to the corresponding trans-15-hydroxy group. With the process from DE-OS 23 57 815 the prior art has a microbiological method, which, for example, converts an 11-hydroxy-15-oxo-prostaglandin to a mixture of 11 alpha, 15 alpha and 11 beta, 15 beta-dihydroxyprostaglandin. The cis-arrangement of the 11 alpha, 15 alpha-hydroxy groups corresponds to those in biologically active prostaglandins.

The method described in DE-OS 24 01 761 fails like all the mentioned processes.

The strains *Kloeckera*, *Saccaromyces* and *Hansenula* mentioned in EP 12710 reduce the 15-keto group in prostacyclin intermediate products only partially and the yields of prostacyclin intermediate products with 15 alpha-hydroxy group are very poor.

It has now been found that the above mentioned prostacyclin intermediate steps in very good yields can be enantioselectively reduced to the corresponding 15 alpha-hydroxy compounds if *Candida* or *Pichia* strains are used for this purpose.

Pharmacologically effective prostacyclins can be produced from 15 alpha hydroxy compounds produced according to the process of the invention by maintaining of the center of asymmetry in the 15 position. For example, starting from (1S, 2S, 3R, 5R)-7,7-ethylenedioxy-3-benzoyloxy-2-[(1E), (4RS)-4-methyl-3-oxo-oct-1-en-6-in-yl]-bicyclo[3.3.0]octane (1) it is possible in a multistage synthesis to arrive at the active substance Iloprost (described in EP 11591)

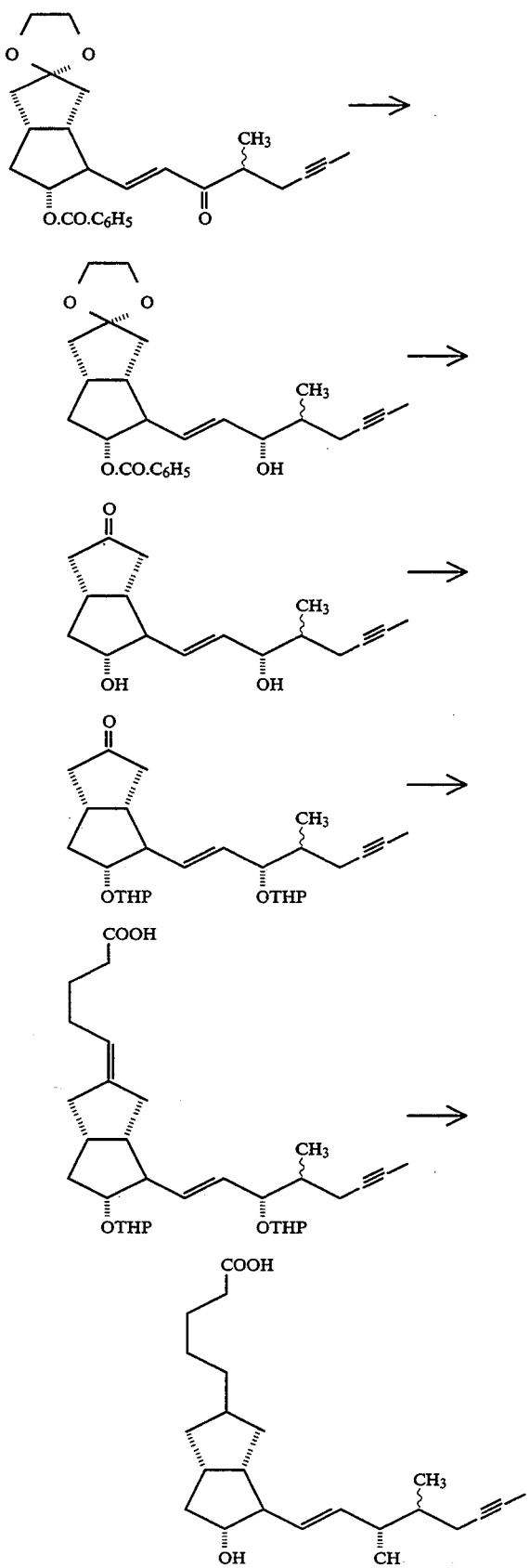

reduction according to the invention naturally occurs. Good results have been obtained from *Candida solani* (NCYC 41), *Candida guilliermondii* (NRRL-y-118) and *Pichia farinosa* (CBS 185), and reductions with the strain *Candida solani* (NCYC 41) produce especially good yields.

The invention therefore relates to a process for enantioselective reduction of the 15-keto group in bicyclic prostaglandin intermediate products to 15 alpha hydroxy compounds of the general formula

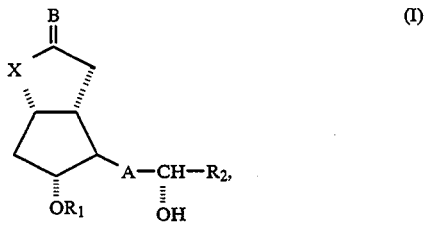

in which

X means oxygen or a $CH_2$ group,

A a trans —CH=CH— or —C≡C— group,

B oxygen the radicals

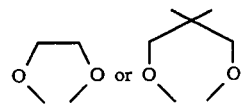

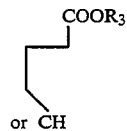

with $R_3$ meaning a $C_1$–$C_4$ alkyl group, $R_1$ hydrogen, tetrahydropyranyl, benzoyl, *tert-butyldimethylgilyl* or *tert-butyldiphenylsilyl* and $R_2$ the radicals

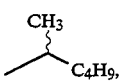

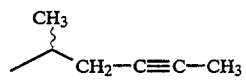

or

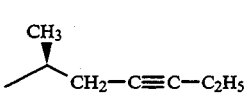

Among the various kinds of indicated classes of microorganisms differences of the effectiveness in the characterized in that a ketone of the general formula II

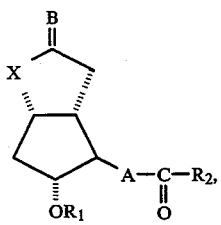

(II)

in which A, B, X, $R_1$ and $R_2$ have the meaning indicated above, is treated with *Candida* or *Pichia* strains and the resulting 15-hydroxyprostaglandin intermediate product is isolated.

By $C_1$–$C_4$ alkyls are understood methyl, ethyl, propyl, isopropyl, butyl, isobutyl, sec-butyl and tert-butyl.

The process works particularly advantageously if $R_1$ in the compounds of formula II means benzoyl.

Depending on the meaning of $R_1$ ultimately desired, the protecting groups can be cleaved off according to methods known in the art.

First, submerged cultures are incubated under culture conditions usually used for said microorganisms in a suitable nutrient medium and with aeration. Then the substrate (dissolved in a suitable solvent or preferably in emulsified form) is added to the cultures and fermented until a maximum conversion of substrate is achieved.

Suitable substrate solvents are, for example, methanol, ethanol, glycol monomethyl ether, dimethylformamide or dimethyl sulfoxide. Emulsification of the substrate can be produced, for example, by the substrate being injected in micronized form or dissolved in a water-miscible solvent (such as methanol, ethanol, acetone, glycol monomethyl ether, dimethylformamide, dimethyl sulfoxide) with strong turbulence in (preferably decalcified) water, which contains the usual emulsification aids. Noniongenic emulsifiers as, for example, ethylene oxide adducts or fatty acid esters of polyglycols are suitable as emulsification aids. Commercial wetting agents Tegin ®, Tagat ® and Span ®, for example, can be mentioned as suitable emulsifiers.

Emulsification of the substrates often makes possible an increased substrate throughput and consequently an increase of the substrate concentration. But, of course, it is also possible in the process according to the invention to use other methods for increasing the substrate throughput, as are well known to the fermentation expert.

The optimal substrate concentration, substrate addition time and fermentation period are dependent on the structure of the substrate used and the type of microorganism used. These magnitudes, as is generally necessary in microbiological conversions, must be determined in the particular case by preliminary tests, as they are familiar to the man of the art.

The strains *Candida solani* (NCYC 41) and *Pichia farinosa* (CBS 185) were deposited at the Deutsche Sammlung von Mikroorganismen (German Collection of Microorganisms) Grisebachstrasse 8, D-3400, Göttingen, West Germany, under numbers DSM 3315 and DSM 3316 on May 21, 1985. *Pichia farinosa* (NRRL-y-118) was deposited in September, 1940 with the Agriculture Research Service Culture Collection (NRRL), Northern Regional Research Center, U.S. Department of Agriculture, 1815 N. University St., Peoria, Ill., 61604.

The following examples of embodiment sere to explain the process according to the invention.

EXAMPLE 1

A 2-liter Erlenmeyer flask, which contains 500 ml of a nutrient solution, sterilized 30 min. at 120° C. in the autoclave, consisting of 1.5% glucose monohydrate, 0.5% yeast extract (Difco), 0.5% corn steep liquor and 0.5% ammonium sulfate, pH adjusted to 6.3, is inoculated with a slant agar culture of the strain *Candida solani* (NCYC 41) and shaken for 2½ days on a rotary shaker at 30° C.

With 250 ml of this incubation culture is inoculated a 20-liter prefermenter which is provided with 15 liters of a nutrient medium, sterilized for 30 min. at 121° C. and 1.1 bars of excess pressure, of the same composition as the incubation culture. With the addition of silicon SH as antifoaming agent it is germinated at 25° C. and 0.7 bar excess pressure with aeration (15 1/min.) and stirring (220 rpm) for 36 hours.

Afterwards 0.9 liter of this prefermenter culture is taken under sterile conditions and a 20-liter main fermenter, which contains 10 liters of sterilized nutrient solution of the same composition as the prefermenter culture, is inoculated with it. After a growing phase of 6 hours under prefermenter conditions a sterilized solution of 4 g of (1S, 2S, 3R, 5R)-7,7-ethylenedioxy-3-benzoyloxy-[(1E), (4RS)-4-methyl-3-oxo-oct-1-en-6-in-yl]-bicyclo[3.3.0]octane is dissolved in 100 ml of dimethylformamide, is added and further stirred and aerated.

After 90 hours of contact time the reaction is ended. The culture broth is extracted 3 times with methyl isobutyl ketone, the extracts are purified and concentrated by evaporation to dryness in a vacuum. The oily residue is taken up in methanol, filtered from the silicone oil and evaporated to dryness. The remaining oily raw product is dissolved in methylene chloride and for further purification is chromatographed over a silica gel column by means of a solvent gradient 5 l hexane/4 l hexane+1 l acetone. As a result 2.75 g of pure (1S, 2S, 3R, 5R)-7,7-ethylenedioxy-3-benzoyloxy-2-[(1E), (3S, 4RS)-3-hydroxy-4-methyl-oct-1-en-6-in-yl]-bicyclo[3.3.0]octane in the form of a colorless oil is obtained.

EXAMPLE 2

Under the conditions indicated in example 1 the strain *Candida guilliermondii* (NRRL-y-118) is used for the desired keto reduction.

EXAMPLE 3

Under the conditions indicated in example 1 the strain *Pichia farinosa* (CBS 185) is used for the desired keto reduction.

EXAMPLE 4

Under the conditions indicated in example 1 compound 3 with the aid of the strain *Candida solani* (NCYC 41) is reduced to the corresponding 15 alpha hydroxy compound.

EXAMPLE 5

Under the conditions indicated in example 1 compound 5 with the aid of the strain *Candida solani* (NCYC 41) is reduced to the corresponding 15-alpha hydroxy compound.

We claim:

1. A process for the production of 15-alpha-hydroxyprostaglandin intermediates of formula I

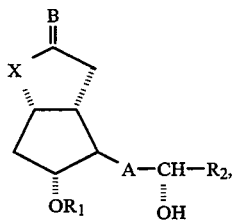

wherein

X is CH₂,

A is trans —CH=CH—[ or —C≡C—],

B is ethylenedioxy or 2,2-dimethylpropylenedioxy,

R₁ is [H, tetrahydropyranyl,] benzoyl, [tert-butyl-dimethylsilyl or tert-butyldiphenylsilyl] and

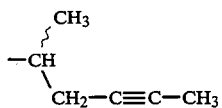

comprising treating a ketone of formula II

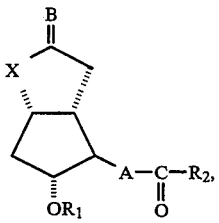

wherein A, B, X, R₁ and R₂ have the meanings indicated above, with a culture of *Candida solani* (NCYC 41) and isolating the resulting 15-alpha-hydroxyprostaglandin intermediate.

2. A method of claim 1, further comprising converting the thus-obtained 15-alpha-hydroxy compound to a pharmacologically effective prostacyclin.

* * * * *

UNITED STATES PATENT AND TRADEMARK OFFICE
CERTIFICATE OF CORRECTION

PATENT NO. : 5,403,724
DATED : April 4, 1995
INVENTOR(S) : Karl PETZOLDT et al.

It is certified that error appears in the above-indentified patent and that said Letters Patent is hereby corrected as shown below:

Title Page; Item [30]   Priority Data

Insert May 29, 1985 [DE] Germany 35 19 548.7

Claim 1; column 7; line 17:  Delete "[ or —C≡C—]".

Column 7, line 19:  Delete "[H, tetrahydropyranyl,]".

Column 7, line 19:  Delete "[tert-butyldimethylsilyl or tert-butyldiphenylsilyl]".

Signed and Sealed this

Twenty-third Day of January, 1996

Attest:

BRUCE LEHMAN

Attesting Officer   Commissioner of Patents and Trademarks